United States Patent [19]

Allcock et al.

[11] 4,374,781

[45] Feb. 22, 1983

[54] ALKYLATED PHOSPHAZENE OLIGOMERS AND METHOD OF PREPARATION

[75] Inventors: Harry R. Allcock; Paul J. Harris, both of State College, Pa.

[73] Assignee: The United States of America as represented by the Secretary of the Navy, Washington, D.C.

[21] Appl. No.: 203,202

[22] Filed: Nov. 3, 1980

Related U.S. Application Data

[62] Division of Ser. No. 78,974, Sep. 25, 1979, Pat. No. 4,258,172.

[51] Int. Cl.$^3$ ................................................ C07F 9/65
[52] U.S. Cl. ............................ 260/543 PN; 528/168
[58] Field of Search .................. 260/543 PN; 528/168

[56] References Cited

U.S. PATENT DOCUMENTS 3,131,207  4/1964  Ratz ............................... 260/543PN
3,453,235  7/1969  Klender .............................. 528/399
4,136,084  1/1979  Dieck et al. ......................... 528/168

Primary Examiner—Natalie Trousof
Assistant Examiner—Vera C. Clarke
Attorney, Agent, or Firm—Robert F. Beers; William T. Ellis; Thomas E. McDonnell

[57] ABSTRACT

Alkylated phosphazene oligomers of the general formula $(NP(X_2))_n NPRH$, wherein X represents chlorine or bromine, R represents a linear or branched alkyl, and n represents an integer from 2 to 8, are prepared by reacting, in a nonoxidizing atmosphere, a perhalopolyphosphazene, a Grignard reagent, and a cuprous complex in solution, followed by the addition of a secondary or tertiary alcohol. Polymers useful as high-temperature elastomers, are prepared from the halo-substituted oligomers by heating them at a temperature from about 200° C. to about 300° C., followed by a reaction with an amine, metal alkoxide, or a metal aryloxide at a temperature from 20° to 200° C.

5 Claims, No Drawings

ALKYLATED PHOSPHAZENE OLIGOMERS AND METHOD OF PREPARATION

This is a division of application Ser. No. 078,974, filed Sept. 25, 1979, now U.S. Pat. No. 4,258,172.

BACKGROUND OF THE INVENTION

The present invention pertains generally to the synthesis of phosphazene oligomers and polymers and in particular to the alkylation of these oligomers and polymers.

Polyphosphazenes break down to yield small rings at temperatures above 200° C., which is significantly higher than the decomposition temperature of most organic polymers. However, the need for polymers with the flexibility, flame retardation, and the resistance to ultraviolet light of polyphosphazenes in uses at temperatures above 200° C. is great.

Thermal stability, along with glass-transition temperature, degree of crystallinity, and melt behavior, are strongly affected by the presence of different substituent groups on the backbone chain. One substituent group, which is very promising, is the alkyl group. Previous attempts at alkylating cyclic or acyclic polyphosphazenes resulted in cleavage of the polyphophazene chain.

SUMMARY OF THE INVENTION

It is therefore an object of the present invention to alkylate polyphosphazenes without cleaving the P-N backbone.

A further object is to alkylate polyphosphazenes inexpensively and quickly.

These and other objects are achieved by the reaction of a perhalopolyphosphazene with an alkyl Grignard reagent in the presence of $Cu^+$ cation to form a metallophosphazene intermediate, followed by a reaction of this intermediate with a hindered alcohol.

DETAILED DESCRIPTION OF THE PRESENT INVENTION

The oligomers of the present invention termed 1-hydrido-1-alkyl-perhalopoly phosphazenes may be cyclic or acyclic, and have the general formula $(NP(X_2))_n$ NPRH wherein X represents chlorine or bromine, R represents a linear or branched alkyl having from 1 to 15 carbon atoms in the backbone chain and preferably having 1 to 4 carbon atoms with 1 to 30 side chains of 1 to 4 carbon atoms, and n represents an integer from 2 to 8.

The oligomers and the corresponding polymers preferred by consideration of cost, availability of starting materials, and yields are 1-hydrido-1-alkyl-tetrachlorocyclotriphosphazene ($N_3P_3Cl_4RH$) and 1-hydrido-1-alkyl-hexachlorocyclotetraphosphazene ($N_3P_4Cl_6RH$) wherein the alkyl group is methyl, ethyl, propyl, and butyl.

The exact reaction pathway that leads to the formation of the metallo-phosphazene intermediate is not completely known, but experimental data indicate that the overall reaction mechanism is the following.

The preparation involving hexachlorocyclotriphosphazene is representative of the general synthesis and is represented by the following schematic:

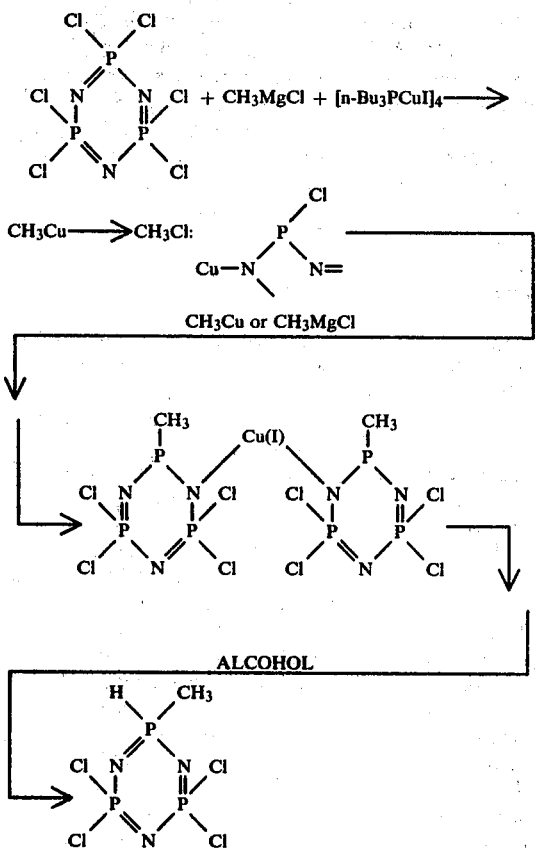

The synthesis begins by admixing in a solvent in a nonoxidizing atmosphere perchloropolyphosphazene and a cuprous complex in a phosphazene-to-copper mole ratio from about 4:1 to about 8:1 and preferably 8:1 at a temperature not exceeding the decomposition temperature of the alkyl copper intermediate. Examples of suitable cuprous complexes are copper iodide (CuI) and trialkylphosphene copper halide tetramer $R_3PCuX_4$, wherein, R represents methyl, ethyl, propyl, butyl, or pentyl and X represents iodide, bromide, or chloride. The solvent must at least completely dissolve the metallo-phosphazene intermediate and have electron-donor characteristics. Preferably, the solvent should dissolve all of the reactants. The preferred solvents are tetrahydrofuran, ethyl ether, and propyl ether. The decomposition temperature of the alkyl copper intermediate can be readily determined by reference to a standard data book. Tertiary alkyl copper compounds are the most unstable and therefore the synthesis is run at −80° C. Primary alkyl copper compounds are the most stable, allowing the synthesis to occur at 0° C. The reaction can proceed as low as −100° C. at an adequate reaction rate.

As the phosphazene and the copper reagent are being stirred, the Grignard reagent is slowly added in a Grignard-to-copper mole ratio from about 24:1 to about 40:1 and preferably 24:1 at a rate which keeps the temperature and reaction under control. Since the production and consumption of the copper alkyl intermediate are almost instantaneous, the temperature can be allowed to rise to about room temperature. In fact the temperature can be raised to about 40° C. Mixing the reactants is continued until the reaction forming the metallo-phosphazene intermediate is complete as determined by, e.g., monitoring the reaction solution with NMR.

A hindered alcohol, e.g., a secondary or tertiary alcohol is added to the reaction mixture at a temperature from about −20° C. to about 30° C. and preferably at 0° C. in an amount at least equal to the amount of phosphazene reactant. Stirring is continued until the reaction is complete, usually about 30 to 60 minutes. The completion can be determined by NMR-monitoring of the reaction solution. The reaction goes to completion quickly. The alkylated phosphazene is isolated by, e.g., removing the solvent in vacuo and subliming or distilling the residue.

This method was reported in P. J. Harris and H. R. Allcock in JACS, September 27, 1978 on p. 6512 and 13 which is incorporated therein by reference.

The following examples are given to illustrate the practice of the present invention. It is understood that the examples are given by way of illustration and are not meant to limit the specification or the claims to follow in any manner.

Hexachlorocyclotriphosphazene was supplied by Ethyl Corporation and was purified by sublimation, followed by 2 recrystallizations from n-hexane. The Grignard reagents were commercial products obtained from Aldrich or Alfa-Ventron. Tetrahydrofuran was distilled into the reaction flask under an atmosphere of dry nitrogen from a sodium-benzophenone ketal drying agent. The reagent, [n-Bu$_3$PCuI]$_4$, was prepared by the method disclosed in G. B. Kauffman and L. A. Teter, Inorg. Synth. I, 9 (1963) and was recrystallized from 2-propanol/ethanol before use. All reactions were carried out under an atmosphere of dry nitrogen.

EXAMPLE I

Synthesis of 1-Hydrido-1-ethyl-tetrachlorocyclotriphosphazene

Hexachlorocyclotriphosphazene (5.0 g, 0.014 mol) and [n-Bu$_3$PCuI]$_4$ (3.0 g, 0.019 mol) were stirred together in tetrahydrofuran (150 ml) at −80° C., and CH$_3$CH$_2$MgCl (10 ml of a 3 M solution in THF) was added dropwise over a period of 30 min. The temperature was allowed to rise to ≃−30° C., and a further 10 ml of CH$_3$CH$_2$MgCl was added. The reaction mixture was then stirred for 16 h and the temperature was allowed to rise to 25° C. The mixture was then cooled to 0° C. and 2-propanol (10 ml) was added. Finally, removal of the solvent in vacuo and sublimation of the residues gave the hydrido-phosphazene in 76% yield.

Yields, analytical data, mass spectral and infrared data are summarized in Table I.

EXAMPLE II

Synthesis of 1-Hydrido-1-t-butyl-tetrachlorocyclotriphosphazene

Hexachlorocyclotriphosphazene (5.0 g, 0.014 mol) and [n-Bu$_3$PCuI]$_4$ (3.0 g, 0.019 mol) were stirred together in tetrahydrofuran (150 ml) at −80° C., and t-butyl magnesium chloride (10 ml of a 3 M solution in ether) was added dropwise over a period of ≃30 min. The temperature was allowed to rise to −30° C., and a further 10 ml of t-butyl magnesium chloride was added. The reaction mixture was then stirred for 16 h and the temperature was allowed to rise to 25° C. The mixture was then cooled to 0° C. and 2-propanol (10 ml) was added. Finally, removal of the solvent in vacuo and sublimation of the residues gave the hydrido-phosphazene in a 70% yield. Yields, analytical data, mass spectral and infrared data are summarized in Table I.

EXAMPLE III

Variation of the Copper Concentration

A series of reactions were carried out in which the amount of phosphazene and added Grignard reagent were maintained constant, but the quantity of copper in the reaction mixture was varied. The amount of (NPCl$_2$)$_3$ used in each case was 5.0 g, with 20 ml of a 3 M solution of methylmagnesium chloride in THF. The reactions were carried out as described previously. The results are summarized in Table II.

EXAMPLE IV

Reaction of (NPCl$_2$)$_3$ with Methylcopper

The reagent, [n-Bu$_3$PCuI]$_4$ (11 g, 0.0069 mol), was dissolved in THF (150 ml) and was cooled to −80° C. Methylmagnesium chloride (10 ml, 3.0 M solution in THF) was then added dropwise. The rapid formation of methylcopper was evident from the deposition of a heavy yellow precipitate. After the mixture had been stirred for 30 min, (NPCl$_2$)$_3$ (5.0 g, 0.014 mol), dissolved in THF (100 ml), was added rapidly to the suspension of methylcopper at −80° C. The reaction was stirred for a further 16 h, during which time the temperature was allowed to rise to 25° C. Finally, (CH$_3$)$_2$CHOH (10 ml) was added to the mixture, which was then stirred for a further 30 min. Removal of the solvent under vacuum and sublimation of the residue gave a mixture of products. These products were analyzed by gas chromatography/mass spectrometry and was found to consist of (NPCl$_2$)$_3$, N$_3$P$_3$Cl$_5$H, and N$_3$P$_3$Cl$_4$(CH$_3$)H.

TABLE I

| Compound | % Yield | M.Pt. | Infrared Data | | Mass Spectral Data | | Elemental Analysis | |
| --- | --- | --- | --- | --- | --- | --- | --- | --- |
| | | | PH | PN | Found[b] | Calculated[c] | Found | Calculated |
| N$_3$P$_3$Cl$_4$(C$_2$H$_5$)H | 60% | 59° | 2399 (m) | 1128 (s) | 305 | 305 | C 7.82 | C 7.82 |
| | | | 2395 (m) | 1185 (s) | | | H 2.00 | H 1.95 |
| | | | | 1170 (sh) | | | N 13.71 | N 13.68 |
| | | | | | | | P 30.39 | P 30.29 |
| | | | | | | | Cl 46.17 | Cl 46.25 |
| N$_3$P$_3$Cl$_4$(i-C$_3$H$_7$)H | 69% | 65° | 2395 (m) | 1210 (s) | 319 | 319 | C 11.34 | C 11.21 |
| | | | 2380 (m) | 1185 (s) | | | H 2.50 | H 2.49 |
| | | | | 1170 (s) | | | N 13.08 | N 13.08 |
| | | | | | | | P 28.75 | P 28.93 |
| | | | | | | | Cl 44.10 | Cl 44.24 |
| N$_3$P$_3$Cl$_4$(t-C$_4$H$_9$)H[d] | 55% | 39° | 2375 (m) | 1245 (s) | 333 | 333 | | |
| | | | 2365 (m) | 1200 (s) | | | | |

TABLE I-continued

| Compound | % Yield | M.Pt. | Infrared Data | | Mass Spectral Data | | Elemental Analysis | |
|---|---|---|---|---|---|---|---|---|
| | | | PH | PN | Found[b] | Calculated[c] | Found | Calculated |
| | | | | 1185 (s) | | | | |

[a]w = weak, m = medium, s = strong, br = broad, sh = shoulder.
[b]As the base peak in a $Cl_4$ isotope pattern.
[c]Calculated using $^{35}Cl_4$.
[d]Elemental analysis could not be obtained on this compound due to its low thermal stability.

TABLE II

| [n-Bu$_3$PCuI]$_4$ Wt. | Cu/Phos. % | Product Yield Wt. | %[a] |
|---|---|---|---|
| 0.28 g | 5 | 0.50 g | 12 |
| 0.84 g | 15 | 0.95 g | 23 |
| 1.40 g | 25 | 1.60 g | 38 |
| 1.96 g | 35 | 2.40 g | 58 |
| 2.52 g | 45 | 2.93 g | 70 |
| 3.08 g | 55 | 3.04 g | 74 |
| 4.20 g | 75 | 3.12 g | 76 |
| 5.50 g | 100 | 3.15 g | 76 |

[a]calculated for $N_3P_3Cl_4(CH_3)H$

Compounds with the following formula: $[NP(Y_2)_nNPRH]_m$, wherein Y represents chlorine, bromine, alkoxy, aryloxy, or amino groups, n is defined as before, and m is an average value and equals any value up to about 15,000, can be prepared from the subject oligomers by standard techniques. The alkoxy group has from 1 to 8 carbon atoms in the backbone chain and from 1 to 4 carbon atoms in any branch. The aryloxy derivative has from 6 to 10 carbon atoms. The alkoxy and aryloxy groups may be substituted with halogen, nitro, or cyano, but the preferred substituent is fluorine. The amino group has from 1 to 8 carbon atoms and can be either a primary or secondary amine. An excellent technique for this polymerization is described in U.S. Pat. No. 3,370,020 issued Feb. 20, 1968 on U.S. Patent Application Ser. No. 400,222 to H. R. Allcock and R. L. Kugel. The polymer has only halogen substituents which can be converted to oxy or amino substituents by standard techniques such as the ones described in U.S. Pat. No. b 3,370,020 or in Allcock, H. R. Inorganic Polymers in Sci. American @ pp. 66–74, March 1974.

The following example is given to illustrate the preparation of the polymers of the present invention. It is understood that this example is given by way of demonstration and is not meant to the specification in any manner.

EXAMPLE V

Two parts of methyl hydrido tetrachloropolyphosphazene were recrystallized from n-heptane, degassed and heated to 250° C. for 4 hours. Polymerization was terminated at this time since a glass ball, one half inch in diameter ceased to flow, due to the increased viscosity of the molten mass, when the vessel was inverted. Termination was effected by cooling the vessel to room temperature. The product was a fluffy rubbery material and upon contact with tetrahydrofuran, the product swelled appreciably.

Obviously many modifications and variations of the present invention are possible inlight of the above teachings. It is therefore to be understood that within the scope of the appended claims the invention may be practiced otherwise than as specifically described.

What is claimed and desired to be secured by Letters Patent of the United States is:

1. A phosphazene oligomer having the formula: $(NP(X_2))_nNPRH$, wherein X represents chlorine or bromine, R represents a linear or branched alkyl, and n represents an integer from 2 to 8.

2. The phosphazene oligomer of claim 1 wherein said oligomer is cyclic.

3. The oligomer of claim 2 wherein said alkyl is linear and has from 1 to 15 carbon atoms.

4. The oligomer of claim 2 wherein said alkyl is branched, has 1 to 15 carbon atoms in the backbone chain, and has from 1 to 30 side chains of 1 to 4 carbon atoms.

5. A method for alkylating phosphazene oligomer which comprises:

admixing, in a solvent, perchloropolyphosphazene and a cuprous complex in a phosphazene-to-copper mole ratio from about 4:1 to about 8:1 in a nonoxidizing atmosphere;

adding, while maintaining mixing, a Grignard reagent in a Grignard-to-copper mole ratio from about 24:1 to about 40:1;

mixing the reactants until a metallo-phosphazene intermediate is formed;

adding a hindered alcohol to said intermediate while mixing is continued; and separating the product.

* * * * *